(12) United States Patent
Hedrick et al.

(10) Patent No.: US 11,739,115 B2
(45) Date of Patent: *Aug. 29, 2023

(54) FUNCTIONALIZED BILE ACIDS FOR THERAPEUTIC AND MATERIAL APPLICATIONS

(71) Applicant: International Business Machines Corporation, Armonk, NY (US)

(72) Inventors: James L. Hedrick, Pleasanton, CA (US); Nathaniel H. Park, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 54 days.

This patent is subject to a terminal disclaimer.

(21) Appl. No.: 17/497,335

(22) Filed: Oct. 8, 2021

(65) Prior Publication Data
US 2022/0024966 A1  Jan. 27, 2022

Related U.S. Application Data

(63) Continuation of application No. 16/785,010, filed on Feb. 7, 2020, now Pat. No. 11,161,870, which is a continuation of application No. 16/351,901, filed on Mar. 13, 2019, now Pat. No. 10,611,792, which is a continuation of application No. 15/816,187, filed on Nov. 17, 2017, now Pat. No. 10,294,265.

(51) Int. Cl.
| | | |
|---|---|---|
| *C07J 9/00* | (2006.01) | |
| *C07J 41/00* | (2006.01) | |
| *C08G 64/42* | (2006.01) | |
| *C08G 73/02* | (2006.01) | |
| *C08G 65/333* | (2006.01) | |
| *C08G 65/331* | (2006.01) | |
| *C08G 64/18* | (2006.01) | |

(52) U.S. Cl.
CPC .............. *C07J 9/00* (2013.01); *C07J 41/0061* (2013.01); *C08G 64/183* (2013.01); *C08G 64/42* (2013.01); *C08G 65/3314* (2013.01); *C08G 65/33327* (2013.01); *C08G 65/33396* (2013.01); *C08G 73/0206* (2013.01)

(58) Field of Classification Search
CPC .......... C07J 9/00; C07J 41/0061; C08G 64/42
See application file for complete search history.

(56) References Cited

U.S. PATENT DOCUMENTS

| | | | |
|---|---|---|---|
| 1,983,414 A | 12/1934 | Stoll et al. | |
| 5,693,769 A | 12/1997 | Kahne et al. | |
| 7,128,895 B2 | 10/2006 | Cavagna et al. | |
| 7,192,946 B2 | 3/2007 | Starke et al. | |
| 7,303,768 B2 | 12/2007 | Yoo | |
| 7,897,563 B2 | 3/2011 | Soane et al. | |
| 9,353,112 B2 | 5/2016 | Goff et al. | |
| 10,294,265 B1 | 5/2019 | Hedrick et al. | |
| 10,611,792 B2 | 4/2020 | Hedrick et al. | |
| 2006/0003976 A1 | 1/2006 | Zhang et al. | |
| 2012/0149732 A1 | 6/2012 | Chucholowski et al. | |
| 2013/0261317 A1 | 10/2013 | Moriarty et al. | |
| 2016/0120880 A1 | 5/2016 | Tirosh et al. | |

OTHER PUBLICATIONS

Zhang et al., ""Bitter-Sweet" Polymeric Micelles Formed by Block Copolymers from Glucosamine and Cholic Acid," DOI: 10.1021/acs.biomac.6b01640 • Publication Date (Web): Jan. 17, 2017, 25 pages.
Shi et al., "A drug-specific nanocarrier design for efficient anticancer therapy," DOI: 10.1038/ncomms8449 |www.nature.com/naturecommunications, Published Jul. 9, 2015, 14 pages.
Devedec et al., "Aggregation Behavior of Pegylated Bile Acid Derivatives," dx.doi.org/10.1021/la303218q | Langmuir 2012, 28, 10 pages.
Travaglini et al., "Between Peptides and Bile Acids: Self-Assembly of Phenylalanine Substituted Cholic Acids," dx.doi.org/10.1021/jp405342v | J. Phys. Chem. B 2013, 117, 10 pages.
Hong et al., "Cardiac RNAi therapy using RAGE siRNA/deoxycholic acid-modified polyethylenimine complexes for myocardial infarction," Biomaterials xxx (2014), 12 pages.
Lee et al., "Enhanced therapeutic efficacy of an adenovirus-PEI-bile-acid complex in tumors with low coxsackie and adenovirus receptor expression," Biomaterials 35 (2014), 12 pages.
Crucho et al., "Formulation of Functionalized PLGA polymeric nanoparticles for targeted drug delivery," doi: 10.1016/j.polymer.2015.04.083, Received Date: Dec. 16, 2014, 26 pages.
Sardon et al., "Homogeneous isocyanate- and catalyst-free synthesis of polyurethanes in aqueous media," DOI: 10.1039/c3gc40319j, Received Feb. 14, 2013, 6 pages.
Sanders et al., "A Simple and Efficient Synthesis of Functionalized Cyclic Carbonate Monomers Using a Versatile Pentafluorophenyl Ester Intermediate," J. Am. Chem. Soc. 2010, 3 pages.
Guan et al., "Preparation and Characterization of Cholic Acid-Derived Antimicrobial Agents with Controlled Stabilities," Organic Letters, 2000, vol. 2, No. 18, pp. 2837-2840.

(Continued)

*Primary Examiner* — Sikarl A Witherspoon
(74) *Attorney, Agent, or Firm* — Amin, Turocy & Watson, LLP

(57) ABSTRACT

The subject disclosure is directed to functionalized bile acids, preparation thereof, and usage thereof for therapeutic and material applications. In one embodiment, a method of generating functionalized bile acid materials can comprise directly activating a carboxylic acid of a bile acid compound using a coupling agent comprising an amide or ester compound, thereby generating an intermediate bile acid derivative material. The method can further comprise attaching a functional group material to the intermediate bile acid derivative material by reacting the functional group material and the intermediate bile acid derivative material, thereby generating a functionalized bile acid material.

19 Claims, 10 Drawing Sheets

(56) References Cited

OTHER PUBLICATIONS

Fukushima et al., "Supramolecular high-aspect ratio assemblies with strong antifungal activity," DOI: 10.1038/ncomms3861, Received Jul. 15, 2013, 9 pages.
Jia et al., "Thermo- and pH-responsive copolymers bearing cholic acid and oligo(ethylene glycol) pendants: selfassembly and pH-controlled release," ACS Appl. Mater. Interfaces, DOI: 10.1021/acsami.5b06909 • Publication Date (Web): Oct. 19, 2015, 20 pages.
Stoltz et al., "Synthesis and Biological Evaluation of Bile Acid Analogues Inhibitory to Clostridium difficile Spore Germination," DOI: 10.1021/acs.jmedchem.7b00295, Received: Feb. 21, 2017, 21 pages.
Luo et al., "Well-Defined, Size-Tunable, Multifunctional Micelles for Efficient Paclitaxel Delivery for Cancer Treatment," Bioconjugate Chem. 2010, 9 pages.
Non-Final Office Action for U.S. Appl. No. 15/816,187, dated Mar. 5, 2018, 47 pages.
"Macromolecule" pp. 1-6; Wikipedia. https://len.wikipedia.org/wiki/Macromolecule. Last Accessed Feb. 28, 2018. 6 pages.
Dorwald, "Side Reactions in Organic Synthesis." 2005, WILEY-VCH Verlag GmbH & Co. KGaA, Weinheim, Preface. p. IX. 4 pages.
Rozansky et al., "Study on the Antibacterial Action of Spermine." Journal of General Microbiology, 1954, 10, pp. 11-16. 6 pages.
Groselj et al., "Synthesis and Preliminary Biological Evaluations of(+)-Isocampholenic Acid-derived Amides." Molecular Diversity. 2016,20 pp. 667-676. 10 pages.
Final Office Action for U.S. Appl. No. 15/816,187, dated Sep. 25, 2018, 28 pages.
Venkataraman et al., "Formation of Disk- and Stacked-Disk-like Self-Assembled Morphologies fromCholesterol-Functionalized Amphiphilic Polycarbonate Diblock Copolymers." Macromolecules, 2013, 46, pp. 4839-4846. 8 pages.
Vasina et al., "Multifunctional Bile Acid Derivatives as Efficient RNA Transporters (Carriers)." Journal of Pharmaceutics & Drug Delivery Research, 2016, 5:2, pp. 2-8. 8 pages.
Joullie et al., "Evolution of Amide Bond Formation." Arkivoc 2010 (viii), pp. 189-250. 62 pages.
Notice of Allowance for U.S. Appl. No. 15/816,187, dated Dec. 21, 2018, 32 pages.
Terao et al.,"Surface Enrichment of Hydrophilic or Hydrophobic Segment for Fine Biointerfaces." Transactions of the Materials Research Society of Japan, 2010, 35(1) pp. 131-134. 4 pages.
Kim et al., "Reverse Thermal Gelling PEG-PTMC Diblock Copolymer Aqueous Solution." Macromolecules, 2007, 40, pp. 5519-5525. 3 pages.
List of IBM Patents or Applications Treated as Related.
Non-Final Office Action received for U.S. Appl. No. 16/351,901 dated Jun. 5, 2019, 140 pages.
Vicens et al., Bioorganic & Medicinal Chemistry, Novel cationic and neutral glycocholic acid and polyamine conjugates able to inhibit transporters involved in hepatic and intestinal bile acid uptake, 2007, 15(6), pp. 1-23, pp. 2359-2367. (Year: 2007).
Glycocholic acid, PubChem, recovered from https://pubchem.ncbi.nlm.nih.gov/ compound/Glycocholic-acid on May 30, 2019, pp. 1-30, Year: 2019.
Non-Final Office Action received for U.S. Appl. No. 16/785,010 dated Apr. 21, 2020, 87 pages.
Zhang et al., "Enhancing the "Stickiness" of Bile Acids to Cross-Linked Polymers: A Bioconjugate Approach to the Design of Bile Acid Sequestrants", Bioconjugate Chemistry, vol. 11, 2000, pp. 397-400.
Valkonen et al., "Bile acid amidoalcohols: simple organogelators", Biosensors & Bioelectronics, vol. 20, 2004, pp. 1233-1241.
Fieser et al., "Cholylamine Esters", Journal of the American Chemical Society, vol. 75, 1953, pp. 6306-6307.
Moon et al., "MSC-based VEGF gene therapy in rat myocardial infarction model using facial amphipathic bile acid-conjugated polyethyleneimine", Biomaterials, vol. 35, 2014, pp. 1714-1754.
Final Office Action received for U.S. Appl. No. 16/785,010 dated Nov. 4, 2020, 65 pages.
Bellini et al., "Antimicrobial activity of cholane compounds", European Journal of Medicinal Chemistry, vol. 18, No. 2, 1983, pp. 191-195.
Joachimiak et al., "Synthesis of novel amide-linked dimers of lithocholic acid", Journal of Chemical Research, vol. 18, No. 2, 2008, pp. 260-265.
Non-Final Office Action received for U.S. Appl. No. 16/785,010 dated May 13, 2021, 17 pages.
U.S. Appl. No. 16/785,010, filed Feb. 7, 2020.
U.S. Appl. No. 16/351,901, filed Mar. 13, 2019.
U.S. Appl. No. 15/816,187, filed Nov. 17, 2017.

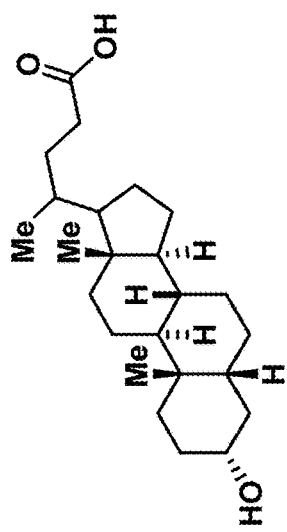
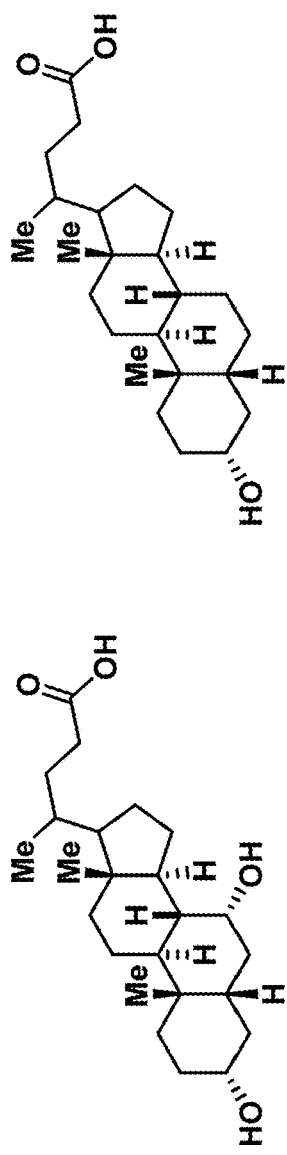
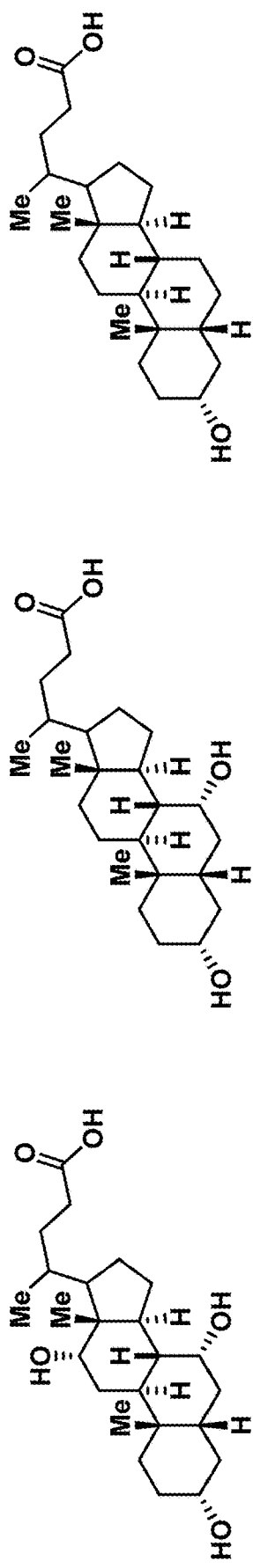
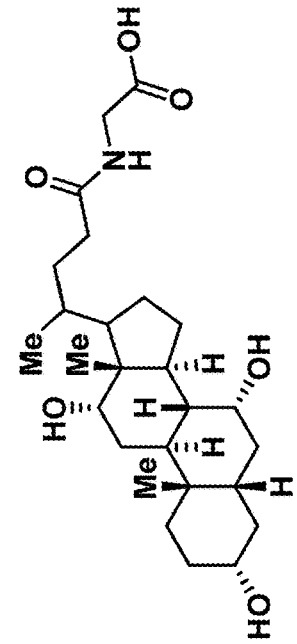
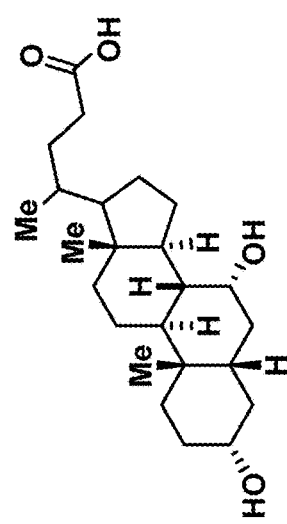
FIG. 1
Example Bile Acids

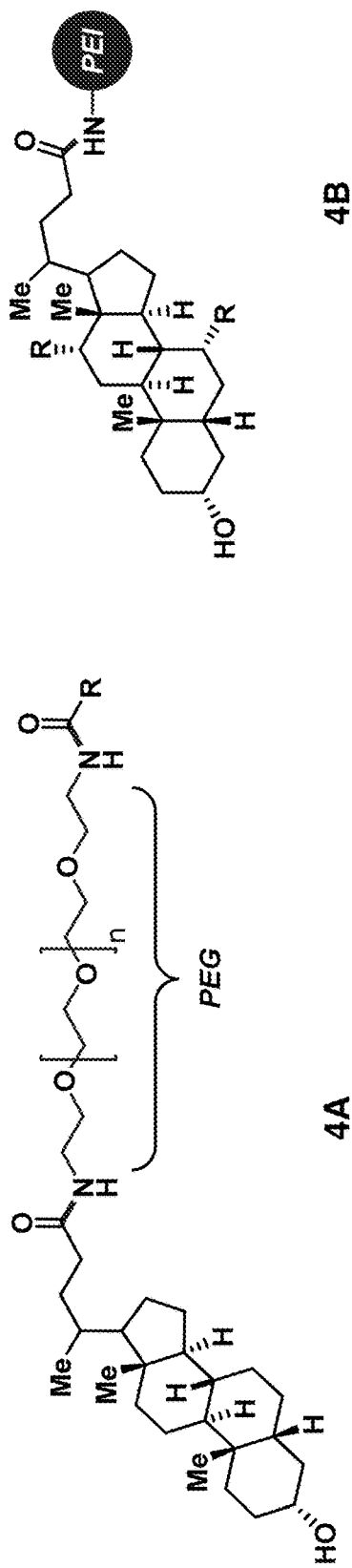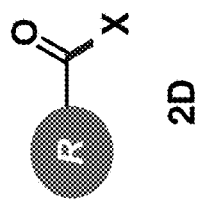
wherein X = a macromolecular amine
FIG. 4

Synthesis Route for Cationic, Bile Acid Functionalized Polycarbonate

FUNCTIONALIZED BILE ACIDS FOR THERAPEUTIC AND MATERIAL APPLICATIONS

TECHNICAL FIELD

This application generally relates to functionalized bile acids, preparation thereof, and usage thereof for therapeutic and material applications.

SUMMARY

The following presents a summary to provide a basic understanding of one or more embodiments of the invention. This summary is not intended to identify key or critical elements, or delineate any scope of the different embodiments or any scope of the claims. Its sole purpose is to present concepts in a simplified form as a prelude to the more detailed description that is presented later. The subject disclosure relates to functionalized bile acids, preparation thereof, and usage thereof for therapeutic and material application.

According to an embodiment, a method is provided for attaching functional groups to bile acids that comprises directly activating a carboxylic acid of a bile acid compound using a coupling agent comprising an amide or ester compound, thereby generating an intermediate bile acid derivative material. The method further comprises attaching a functional group material to the intermediate bile acid derivative material by reacting the functional group material and the intermediate bile acid derivative material, thereby generating a functionalized bile acid material. In various embodiments, the coupling agent comprises pentafluorophenyl carbonate.

In some implementations, the functional group material comprises a small molecule, particularly a small molecule amine. With these implementations, the functionalized bile acid material generated based on reaction of the small molecule amine and the intermediate bile acid material comprises a bile acid amide. In one embodiment, the method can further comprise attaching a polymer to a functional group of the bile acid amide, thereby generating a functionalized bile acid polymer. In other implementations, the functional group material can comprise a macromolecular amine, thus making the resulting functionalized bile acid material a bile acid macromolecule amide.

In various embodiments, the functional group material can comprise a polymer that provides therapeutic properties. With these embodiments, the functionalized bile acid material can be therapeutic material itself or serve as a therapeutic material carrier. In another implementation, the functional group material can comprise a polymer that has disinfectant properties, thereby making the functional bile acid material a disinfectant. Further, in some implementations in which the functional group material comprises a polymer that makes the functionalized bile acid material therapeutic material or a therapeutic material carrier, the functionalized bile acid material can cross a blood brain barrier in association with providing therapeutic functionality.

In another embodiment, a functionalized bile acid material is provided that comprises a chemical structure of Structure I:

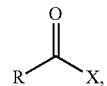

Structure I wherein R comprises a bile acid steroid backbone, and
wherein X comprises a polymer.

In some implementations, the polymer X comprises an amine terminated polymer. In another implementation, the polymer X comprises a material selected from the group comprising polyethylene glycol and polyethylene amine. In another implementation, the polymer can comprise a diblock polycarbonate copolymer. For example, in accordance with this implementation, the functionalized bile acid material can comprise the chemical structure II:

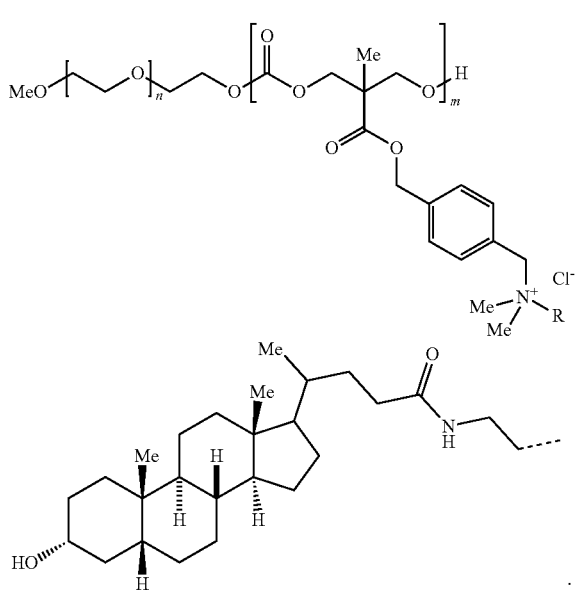

Structure II

In another embodiment, a method is provided that comprises generating an intermediate bile acid derivative material by directly activating a carboxylic acid of a bile acid compound using a coupling agent comprising an amide or ester compound. The method further comprises generating a functionalized bile acid material using the intermediate bile acid derivative material, wherein the functionalized bile acid material comprises a chemical structure of structure I:

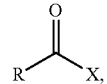

Structure I wherein R comprises a bile acid steroid backbone, and
wherein X comprises a nucleophile selected from a group consisting of small molecule amines and macromolecular amines.

In various implementations, the coupling agent comprises pentafluorophenyl carbonate. In some implementations, the process of generating the functionalized bile acid material comprises attaching the amine nucleophile X to the intermediate bile acid derivative material by directly reacting the nucleophile with the intermediate bile acid derivative material. Reaction of the intermediate bile acid derivative material with the amine nucleophile X renders the resulting functionalized bile acid material having Structure I a bile acid amide.

In another implementation, the method further comprising, generating a functionalized bile acid polymer using the functionalized bile acid material having structure I. With this implementation, the method can further comprise attaching the functionalized bile acid material having Structure I to a polymer via a functional group of the nucleophile X, thereby generating the corresponding functionalized bile acid polymer. For example, in accordance with one implementation in which the nucleophile X comprises an amide functional group, a diblock polycarbonate copolymer can be attached to the functionalized bile acid material (or vice versa) via the amide functional group, resulting in a functionalized bile acid polymer comprising chemical Structure II:

Structure II

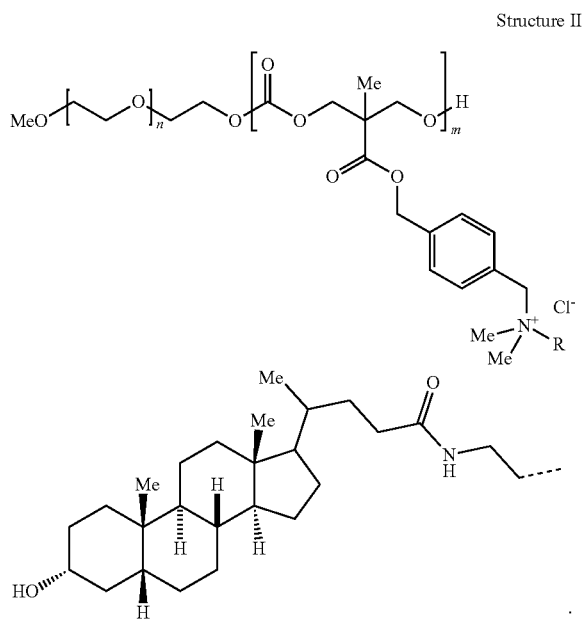

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIG. 1 presents example, non-limiting structures of different bile acids in accordance with various aspects and embodiments described herein.

FIG. 4 presents some example, non-limiting macromolecular bile acid amides generated based on functionalization of a bile acid with different macromolecular amines in accordance with various aspects and embodiments of the subject disclosure.

DETAILED DESCRIPTION

Figure 2:
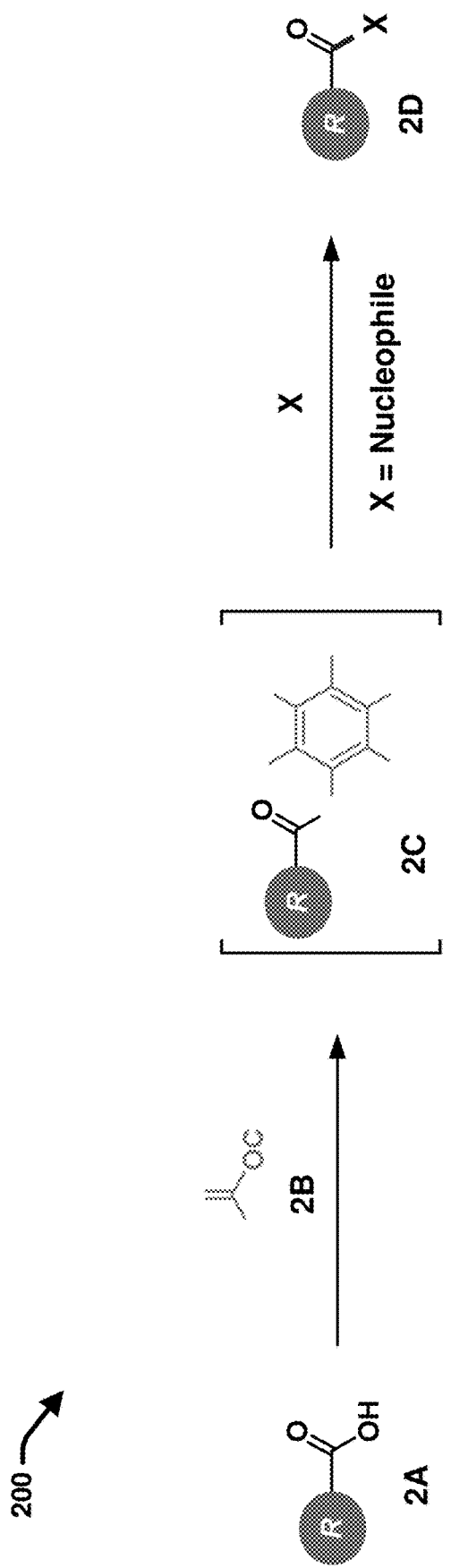
FIG. 2 presents an example, non-limiting synthesis route for generating functionalized bile acid materials in accordance with various aspects and embodiments described herein.

The following detailed description is merely illustrative and is not intended to limit embodiments and/or application or uses of embodiments. Furthermore, there is no intention to be bound by any expressed or implied information presented in the preceding Summary section or in the Detailed Description section.

The subject disclosure relates to functionalized bile acids, preparation thereof, and usage thereof for therapeutic and material applications. Bile acids are naturally occurring steroidal compounds that aid in the solubilizing and transport of dietary fats. Their function as emulsifiers stems from the presence of polar functional groups such as carboxylic acids and hydroxyl groups on the otherwise non-polar steroid backbone, affording amphiphilic properties to bile acids. The subject disclosure provides effective strategies for the preparation of functionalized bile acid materials that exploit the amphiphilic nature of bile acids. In this regard, the subject disclosure provides a robust synthetic protocol for the preparation of a wide array of bile acid functionalized materials and macromolecules using a simple amide coupling procedure based on the use of the commercially available pentafluorophenyl carbonate. In particular, the pentafluorophenyl carbonate can be used as an amide and ester coupling agent for the direct synthesis of bile acid functionalized materials and conjugates of bile acids with small molecule amines. This coupling reaction is compatible with a large variety of macromolecular and small molecule amines as well as both primary or secondary amines.

In one or more embodiments, the carboxylic acid of a bile acid can be directly activated by treatment with the pentafluorophenyl carbonate in the presence of base to generate the corresponding pentafluorophenyl ester. The in situ generated pentafluorophenyl ester can then be directly reacted with a variety of primary and secondary amines to produce the corresponding bile acid amides. Using this approach, a variety of small molecule amines can be used to generate the corresponding bile acid amides. Macromolecular amines can also be utilized to produce the corresponding bile acid functionalized macromolecules. Finally, the prepared bile acid amides can be used for the post-synthesis functionalization of polymers.

The use of pentafluorophenyl carbonate is highly advantageous due to its ease of handling and low toxicity compared to standard amide based coupling reagents typically used in the preparation of bile acid materials. In addition, by using pentafluorophenyl carbonate as a coupling agent, the disclosed techniques for preparing bile acid materials do not result in undesirable byproducts, such as urea, that are difficult to remove and typically generated in traditional amide coupling reactions. Further, by using pentafluorophenyl carbonate as the coupling agent, no additional activating agent such as 1-hydroxybenzotriazole or N-hydroxysuccinimide are required, reducing the number of impurities and byproducts that must be removed during the work-up and purification. Finally, the short reaction times and straightforward reaction setup make this approach a highly desirable alternative to preparing both bile acid small molecule conjugates and bile acid functionalized materials.

The resulting functionalized bile acid materials can provide various material applications. For example, in some embodiments, the bile acid materials can provide biomedical applications, including application as therapeutic carriers and therapeutics themselves. For example, one or more bile acid materials generated using the disclosed techniques can be used as vehicles for medication delivery, ribonucleic acid (RNA) delivery, and the formation of polymer-virus complexes for cancer therapy. In some embodiments, by exploiting the ability for bile acids to pass through epithelial layers in association with transporting nutrients and vitamins into the blood stream, one or more of the disclosed bile acid derivative materials can provide biomedical applications that involve providing therapeutics that can cross the blood brain barrier. Further, small molecule bile acid derivatives that can be synthesized using the disclosed techniques can provide self-assembly properties or be utilized as antimicrobial agents.

Various embodiments of the subject disclosure describe techniques for synthesizing bile acid derivative materials. The subject disclosure provides some example laboratory processes that were used to synthesize some of the subject bile acid derivatives. These example laboratory procedures are respectively identified as Synthesis Example 1, Synthesis Example 2, Synthesis Example 3, Synthesis Example 4, Synthesis Example 5 and Synthesis Example 6. These example laboratory synthetization procedures were respectively carried out on the benchtop using benchtop solvents unless otherwise noted. All commercially available reagents and solvents were used as received. The $^1$H- and $^{13}$C-NMR spectra of monomers and polymers were recorded using a Bruker Avance 400 spectrometer, operated at 400 and 100 MHz respectively, with the solvent proton signal as the internal reference standard.

It should be appreciated however that the example laboratory process described with respect to Synthesis Example 1, Synthesis Example 2, Synthesis Example 3, Synthesis Example 4, Synthesis Example 5 and Synthesis Example 6 are intended merely to demonstrate one example synthetization procedure that can be employed to generate corresponding bile acid derivative materials. In this regard, at least some of the reagents, solvents, material concentrations, temperatures, durations, and procedural conditions described with respect to the example laboratory procedures employed can vary.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 presents some example chemical structures 1A, 1B, 1C, 1D and 1E of different bile acids accordance with various aspects and embodiments described herein. As shown in FIG. 1, the bile acids respectively include one or more polar functional groups such as carboxylic acids and hydroxyl groups on an otherwise non-polar steroid backbone, affording them amphiphilic properties.

FIG. 2 presents an example synthesis route 200 for generating functionalized bile acid materials in accordance with various aspects and embodiments described herein. In the embodiment shown, the carboxylic acid group of a bile acid 2A can be directly activated by treatment with the pentafluorophenyl carbonate 2B in the presence of a base to generate an intermediate bile acid derivative material; the corresponding pentafluorophenyl ester 2C. Some suitable base materials that can be employed include but are not limited to: triethylamine, diisopropylethylamine, 1,8-Diazabicyclo[5.4.0]undec-7-ene, or potassium carbonate. In one or more embodiments, the pentafluorophenyl ester 2C can be generated in situ. The bile acid 2A can vary. For example, the bile acid 2A can include any of the bile acids shown in FIG. 1 as well as other existing bile acids. The portion of the bile acid 2A represented by the variable R corresponds to the steroid backbone of the bile acid.

The pentafluorophenyl ester 2C can then be directly reacted with a variety of nucleophiles X to generate the resulting functionalized bile acid material 2D having the following chemical structure I:

Structure I wherein R comprises a bile acid steroid backbone, and wherein X comprises a nucleophile.

In one or more embodiments, the nucleophile X can include various primary and secondary amines, thereby making the resulting functionalized bile acid material 2D a bile acid amide. In this regard, the small molecule amine can be attached to the pentafluorophenyl ester via an amide bond (or an amide bond forming reaction). Using this approach, a variety of small molecule amines can be used as the nucleophile X to generate the corresponding bile acid amides. For example, some example suitable primary amines that can be employed as the nucleophile X can include but are not limited to: ethanolamine, N,N-dimethylethylenediamine, 1-(3-aminopropyl)imidazole, benzylamine, or 2-Amino-2-methylpropane-1,3-diol. Some example suitable secondary amines that can be employed as the nucleophile X can include but are not limited to: diethanolamine, N,N,N'-trimethylethylenediamine, morpholine, 1-methylpiperazine, or 3,3'-iminobis(N,N-dimethylpropyl amine).

Figure 3:
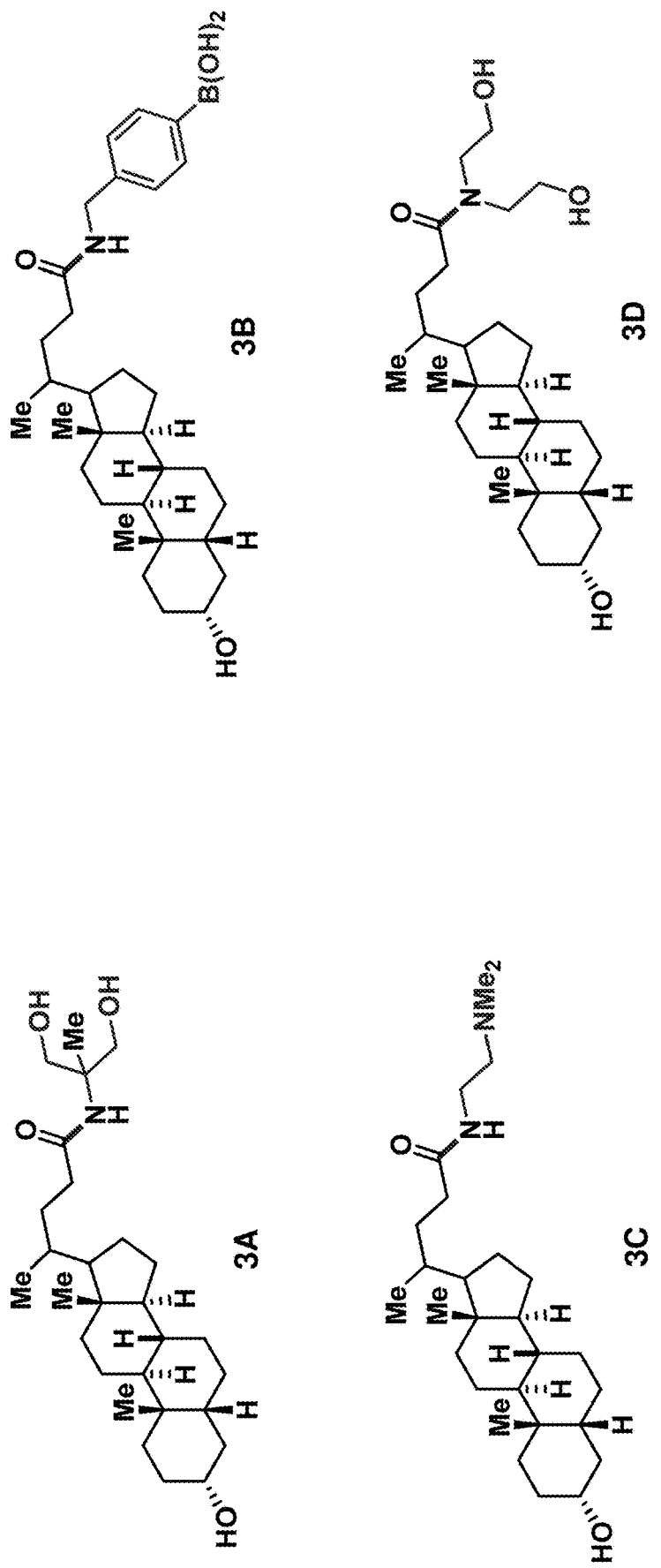
FIG. 3 presents some example, non-limiting bile acid amides generated based on functionalization of a bile acid with different small molecule amines in accordance with various aspects and embodiments of the subject disclosure.

FIG. 3 presents some example bile acid amides 3A, 3B, 3C and 3D that can be generated based on functionalization of a bile acid (e.g., bile acid 2A) with different small molecule amines in accordance with various aspects and embodiments of the subject disclosure. In the embodiment shown, the bile acid amides 3A, 3B, 3C and 3D respectively comprise different small molecule amines attached to the carboxylic acid portion of a bile acid. In this regard, the nucleophile X can comprise a small molecule amine.

With reference again to FIG. 2, one example implementation of synthesis route 200 was carried out to generate a functionalized bile acid material having structure I as follows:

A vial equipped with a magnetic stir bar was charged with bile acid (1.0 equivalent), pentafluorophenyl carbonate (1.0 equivalent), and $CH_2Cl_2$ (1.0 M). The reaction mixture was stirred at room temperature and $Et_3N$ (1.2 equivalent) was added. The reaction mixture became homogenous and carbon dioxide was liberated. The reaction mixture was stirred at room temperature for an additional 1 hour and the amine (1.2 equivalent) was added. The reaction was stirred for an additional 3-18 hours before being subjected to workup and purification.

Synthesis Example 1

Synthesis Example 1 describe one example general procedure for the functionalization of bile acids in accordance with synthesis route 200. It should be appreciated however that Synthesis Example 1 is merely intended to demonstrate one example synthetization procedure that can be employed to generate the corresponding bile acid derivative material having Structure I. In this regard, at least some of the reagents, solvents, material concentrations, temperatures, durations, and procedural conditions described can vary. Further, Synthesis Example 1 is not intended to limit the scope of synthesis route 200.

In one or more additional embodiments, the nucleophile X of structure I can comprise a macromolecular amine. In this regard, the macromolecular amine can be attached to the pentafluorophenyl ester via an amide bond (or an amide bond forming reaction). With these embodiments, synthesis route 200 can also be utilized to produce functionalized bile acid macromolecule amides. Some suitable macromolecular amines that can be employed as the nucleophile X of Structure I can include but are not limited to: α,ω-PEG diamine, polyethyleneimine, or jeffamines.

For example, FIG. 4 presents some example macromolecular bile acid amides 4A and 4B that can be generated based on functionalization of a bile acid with different macromolecular amines in accordance with various aspects and embodiments of the subject disclosure. In the embodiment shown, the macromolecular amine used to generate the corresponding macromolecule bile acid amide 4A using synthesis route 200 comprises polyethylene glycol (PEG), an amine terminated polymer. The number average molecular weight ($M_n$) of the PEG chain can vary. For example, in one implementation, the PEG chain can be about 4600 $M_n$. In another implementation, the PEG can be 8000 $M_n$. The macromolecular amine used to generate the corresponding macromolecular bile acid amide 4B using synthesis route 200 comprises branched polyethylenimine (PEI), another amine terminated polymer. The size of the PEI used can also vary. For example, in one implementation, the PEI can have an $M_n$ of about 10,000. The bile acids used to generate the macromolecular bile acid amides 4A and 4B can also vary. For example, in one implementation, the molecule represented by the variable R in the macromolecular bile acid amides 4B can hydrogen. In another implementation, the R can represent a hydroxyl group. In one or more embodiments, the macromolecular bile acid amides 4A and 4B can be used as therapeutic carriers.

One example implementation of synthesis route 200 was carried out to generate the macromolecular bile acid amide 4A with an $M_n$ of 4600 as follows:

Following the above described Synthesis Example 1 for generating the functionalized bile acid material 2D in accordance with synthesis route 200, a vial was charged with lithocholic acid (103 mg, 0.27 mmol), pentafluorophenyl carbonate (107 mg, 0.27 mmol), and $CH_2Cl_2$ (1 mL). $Et_3N$ (42 μL, 0.30 mmol) was added and the reaction mixture became homogenous. After stirring at room temperature for 2 h, amine-terminated PEG ($M_n$=4600, 500 mg, 0.11 mmol) was added and the reaction mixture was stirred at room temperature for 24 hours. The reaction mixture was then transferred to a dialysis bag (1000 MWCO) and dialyzed against $CH_2Cl_2$:MeOH (1:1) for 24 hours, changing the solvent three times. After dialysis, the polymer was precipitated twice from $Et_2O$ to isolate the desired lithocholic acid functionalized PEG (95% functionalization). $^1H$ NMR ($CDCl_3$) δ 6.05 (m, 1H), 3.64 (m, 410H), 3.45 (m, 7H), 2.24 (m, 2H), 2.07 (m, 2H), 1.80-1.52 (m, 24H), 1.40-1.05 (m, 34H), 0.91 (m, 12H), 0.63 (m, 6H).

Synthesis Example 2

One example implementation of synthesis route 200 was carried out to generate the macromolecular bile acid amide 4A with an $M_n$ of 8000 as follows:

Following the above described Synthesis Example 1 for generating the functionalized bile acid material 2D in accordance with synthesis route 200, a vial was charged with lithocholic acid (103 mg, 0.27 mmol), pentafluorophenyl carbonate (107 mg, 0.27 mmol), and $CH_2Cl_2$ (1 mL). $Et_3N$ (42 μL, 0.30 mmol) was added and the reaction mixture became homogenous. After stirring at room temperature for 2 h, amine-terminated PEG ($M_n$=8000, 500 mg, 0.11 mmol) was added and the reaction mixture was stirred at room temperature for 24 hours. The reaction mixture was then transferred to a dialysis bag (1000 MWCO) and dialyzed against $CH_2Cl_2$:MeOH (1:1) for 24 hours, changing the solvent three times. After dialysis, the polymer was precipitated twice from $Et_2O$ to isolate the desired lithocholic acid functionalized PEG (80% functionalization). $^1H$ NMR ($CDCl_3$) δ 6.05 (m, 1H), 3.64 (m, 719H), 3.45 (m, 10H), 2.24 (m, 2H), 2.07 (m, 2H), 1.80-1.52 (m, 24H), 1.40-1.05 (m, 28H), 0.91 (m, 10H), 0.63 (m, 5H).

Synthesis Example 3

One example implementation of synthesis route 200 was carried out to generate the macromolecular bile acid amide 4B wherein the variable R comprises hydrogen was carried out as follows:

Following the above described Synthesis Example 1 for generating the functionalized bile acid material 2D in accordance with synthesis route 200, a vial was charged with lithocholic acid (147 mg, 0.36 mmol), pentafluorophenyl carbonate (142 mg, 0.36 mmol), and DMF (3 mL). $Et_3N$ (60 μL, 0.43 mmol) was added and the reaction mixture was stirred for 2 hours at room temperature. After 2 hours, the reaction mixture was added via syringe to a stirred solution of branched PEI ($M_n$=10000, 400 mg, 0.04 mmol) in DMF (3 mL) and stirred at room temperature for 24 hours. The reaction mixture was then transferred to a dialysis bag (1000 MWCO) and dialyzed against $CH_2Cl_2$:MeOH (1:1) for 24 hours, changing the solvent three times. Following dialysis, the solvent was removed to afford the lithocholic acid functionalized branched PEI. ¹H NMR (MeOD) δ 3.51 (m, 2H), 3.41 (m, 2H), 2.86-2.63 (m, 91H), 2.22 (m, 2H), 2.06 (m, 2H), 1.96 (m, 1H), 1.85 (m, 1H), 1.70 (m, 3H), 1.57 (m, 2H), 1.38 (m, 8H), 1.28-0.98 (m, 15H), 0.91 (m, 6H), 0.65 (m, 3H).

Synthesis Example 4

One example implementation of synthesis route 200 was carried out to generate the macromolecular bile acid amide 4B wherein the variable R comprises a hydroxyl was carried out as follows:

Following the above described Synthesis Example 1 for generating the functionalized bile acid material 2D in accordance with synthesis route 200, a vial was charged with cholic acid (147 mg, 0.36 mmol), pentafluorophenyl carbonate (142 mg, 0.36 mmol), and DMF (3 mL). Et₃N (60 µL, 0.43 mmol) was added and the reaction mixture was stirred for 2 hours at room temperature. After 2 hours, the reaction mixture was added via syringe to a stirred solution of branched PEI ($M_n$=10000, 400 mg, 0.04 mmol) in DMF (3 mL) and stirred at room temperature for 24 hours. The reaction mixture was then transferred to a dialysis bag (1000 MWCO) and dialyzed against CH₂Cl₂:MeOH (1:1) for 24 hours, changing the solvent three times. Following dialysis, the solvent was removed to afford the cholic acid functionalized branched PEI. ¹H NMR (MeOD) δ 3.95 (m, 1H), 3.79 (m, 1H), 3.48-3.13 (m, 10H), 2.83-2.64 (m, 118H), 2.27 (m, 4H), 1.90-1.79 (m, 10H), 1.58-1.29 (m, 14H), 1.13-0.95 (m, 6H), 0.92 (m, 3H), 0.71 (m, 3H).

Synthesis Example 5

Synthesis Examples 2-5 describe respectively describe example procedures for generation of macromolecular bile acid amides in accordance with synthesis route 200. It should be appreciated however that Synthesis Examples 2-5 are merely exemplary and at least some of the reagents, solvents, material concentrations, temperatures, durations, and procedural conditions described can vary. Further, Synthesis Examples 2-5 are not intended to limit the scope of synthesis route 200.

With reference again to FIGS. 1 and 3, in some implementations, the bile acid amides having chemical structure I above, wherein X comprises a small molecule amine (e.g., bile acid amides 3A, 3B, 3C, and 3D), can be used as disinfectants. In other implementations, the prepared bile acid amides can be used for the post-synthesis functionalization of polymers. With these implementations, a bile acid amide (e.g., bile acid amides 3A, 3B, 3C, 3D and the like), can be attached to the polymer backbone via a functional group of the small molecule amine. In this regard, the amide bond forming reaction between the small molecule amine and the pentafluorophenyl ester 2C can be used to combine the bile acid 2A with an amine having one or more specific functional groups which can then be attached to different polymer backbones.

Figure 5:
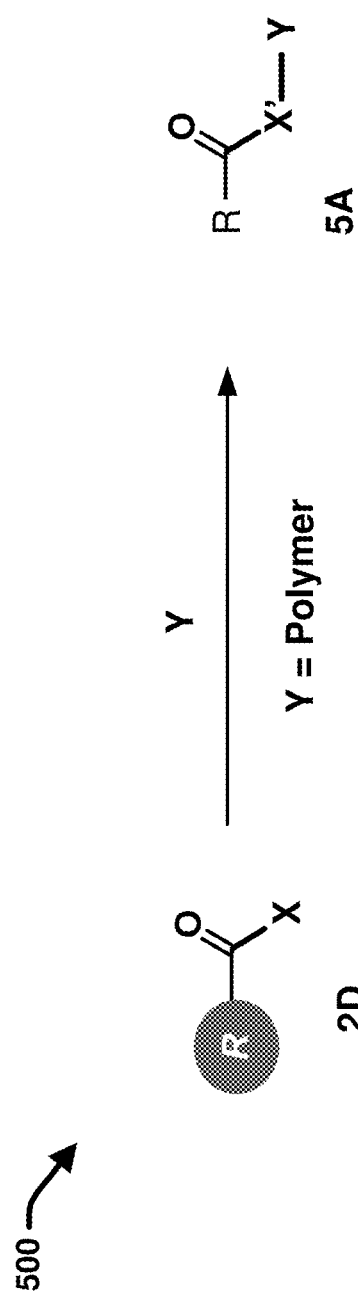
FIG. 5 presents an example, non-limiting synthesis route for generating functionalized bile acid polymers in accordance with various aspects and embodiments described herein.

For example, FIG. 5 presents an example synthesis route for 500 generating functionalized bile acid polymers in accordance with various aspects and embodiments described herein. In the embodiment shown, the functionalized bile acid material 2D having structure I above, (wherein X comprises a small molecule amine), can be directly reacted with a polymer Y to generate the corresponding functionalized bile acid polymer 5A having the following chemical structure III:

Structure III wherein R comprises a bile acid steroid backbone,
wherein X' comprises a reacted nucleophile, and
wherein Y comprises a polymer.

The polymer Y can vary. For example, in one or more embodiments, the polymer Y can include any suitable polymer having the following properties that include having a requisite functional group handle to enable incorporation of a functionalized bile acid. These groups may include, but not limited to: azides, alkynes, alkyl halides, benzyl halides, thioethers, disulfides, epoxides, thiols, alcohols, diols, esters, or boronic acids. For example, the polymer Y can include but is not limited to: polycarbonates, polyurethanes, polylysines, polyethyleneimines, polyionenes, polyacrylates, or other appropriately functionalized polymer. The reacted nucleophile X' corresponds to a nucleophile having a functional group that been attached to the polymer backbone via reaction of the functionalized bile acid material 2D with the polymer Y. In one embodiment, a new bile acid functionalized polymer that provides anti-cancer therapeutic functionality can be generated using synthesis routes 200 and 500. This new bile acid functionalized polymer comprises a cationic, bile acid functionalized polycarbonate compound and is referred to herein as lithocholic acid functionalized polycarbonate.

Figure 6:
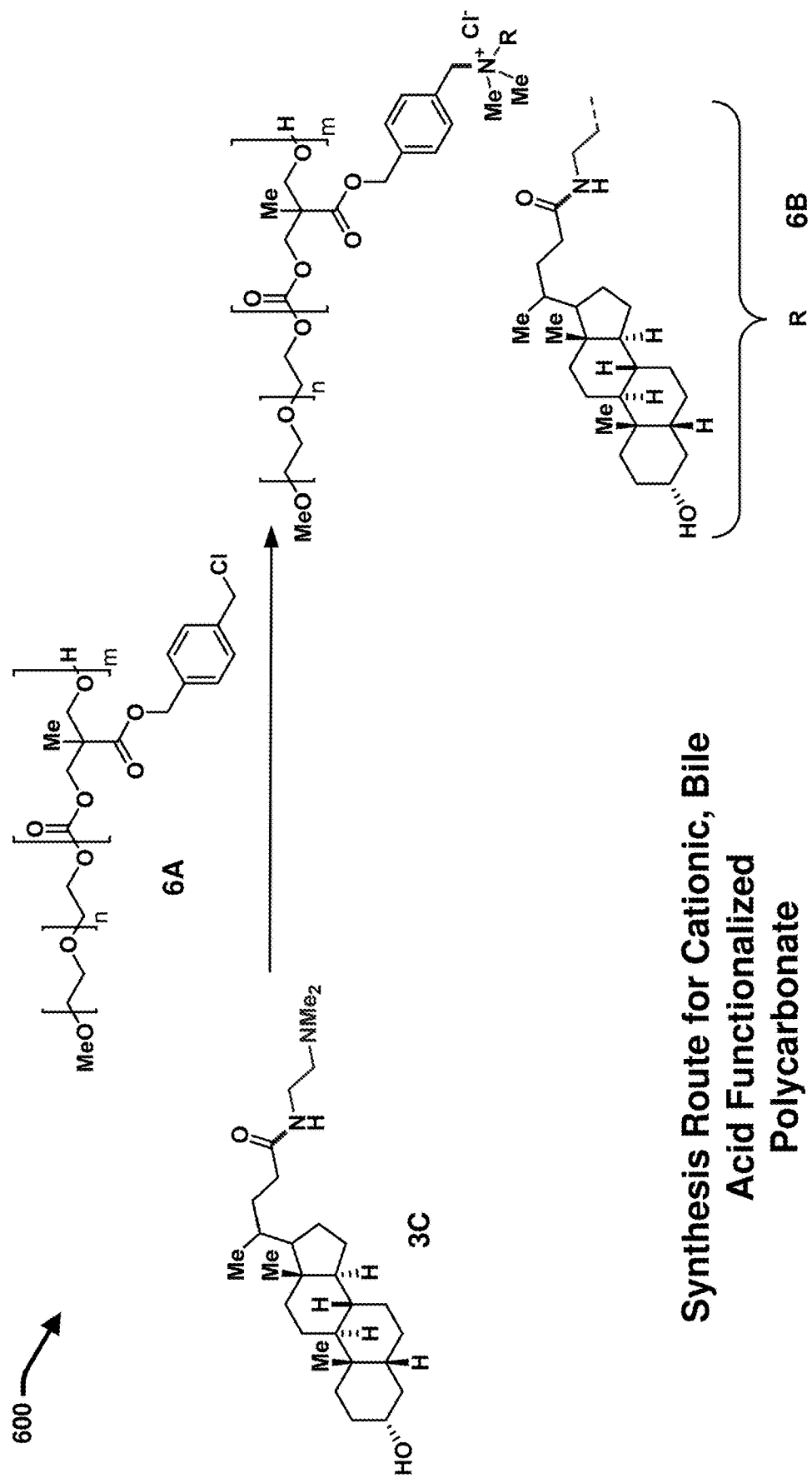
FIG. 6 presents an example, non-limiting synthesis route for generating a cationic, bile acid functionalized polycarbonate compound in accordance with various aspects and embodiments described herein.

FIG. 6 presents an example synthesis route 600 for generating a lithocholic acid functionalized polycarbonate in accordance with various aspects and embodiments described herein. In the embodiment shown, the bile acid amide 3C can be directly reacted with AB diblock polycarbonate copolymer 6A (e.g., a copolymer comprising PEG and polycarbonate) to generated the resulting lithocholic acid functionalized polycarbonate 6B, a cationic, bile acid functionalized polycarbonate compound. In this synthesis route 600, the nitrogen dimethyl or dimethylamine (NMe₂) functional group of the bile acid amide 3C can be quaternized to attach it to the dependent chlorobenzene of the copolymer 6A, thereby resulting in the lithocholic acid functionalized polycarbonate 6B.

One example implementation of synthesis route 500 was carried out to generate the lithocholic acid functionalized polycarbonate 6B, was carried out as follows:

A vial equipped with a magnetic stir-bar was charged with the bile acid amide 3C (100 mg) and the copolymer 6A (112 mg, 0.25 mmol). MeCN (2 mL) and CH₂Cl₂ (1 mL) were added and the reaction mixture was heated to 50° C. in a sand bath for 18 hours. After cooling to room temperature, the reaction mixture was then transferred to a dialysis bag (1000 MWCO) and dialyzed against CH₂Cl₂:MeOH (1:1) for 24 hours, changing the solvent three times. Following dialysis, the solvent was removed to afford the lithocholic acid functionalized polycarbonate 6B (>95% functionalization). ¹H NMR (DMSO) δ 7.58 (m, 20H), 7.46 (m, 20H), 5.18 (m, 26H), 4.60-4.50 (m, 30H), 4.23-4.11 (m, 40H), 3.51 (m, 452H), 3.24 (m, 3H), 3.00 (m, 48H), 2.12 (m, 10H), 2.03 (m, 10H), 1.91 (m, 10H), 1.77-1.51 (m, 65H), 1.33-1.01 (m, 169H), 0.86 (m, 58H), 0.59 (m, 26H).

Synthesis Example 6

Synthesis Example 6 describes one example procedures for the generation of the lithocholic acid functionalized polycarbonate 6B in accordance with synthesis route 500. It should be appreciated however that Synthesis Example 6 is merely exemplary and at least some of the reagents, solvents, material concentrations, temperatures, durations, and procedural conditions described can vary. Further, Synthesis Examples 6 is not intended to limit the scope of synthesis route 500.

FIGS. 7-10 illustrate various methodologies in accordance with the disclosed subject matter. While, for purposes of simplicity of explanation, the methodologies are shown and described as a series of acts, it is to be understood and appreciated that the disclosed subject matter is not limited by the order of acts, as some acts can occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts can be required to implement a methodology in accordance with the disclosed subject matter. Repetitive description of like elements employed in respective embodiments is omitted for sake of brevity.

Figure 7:
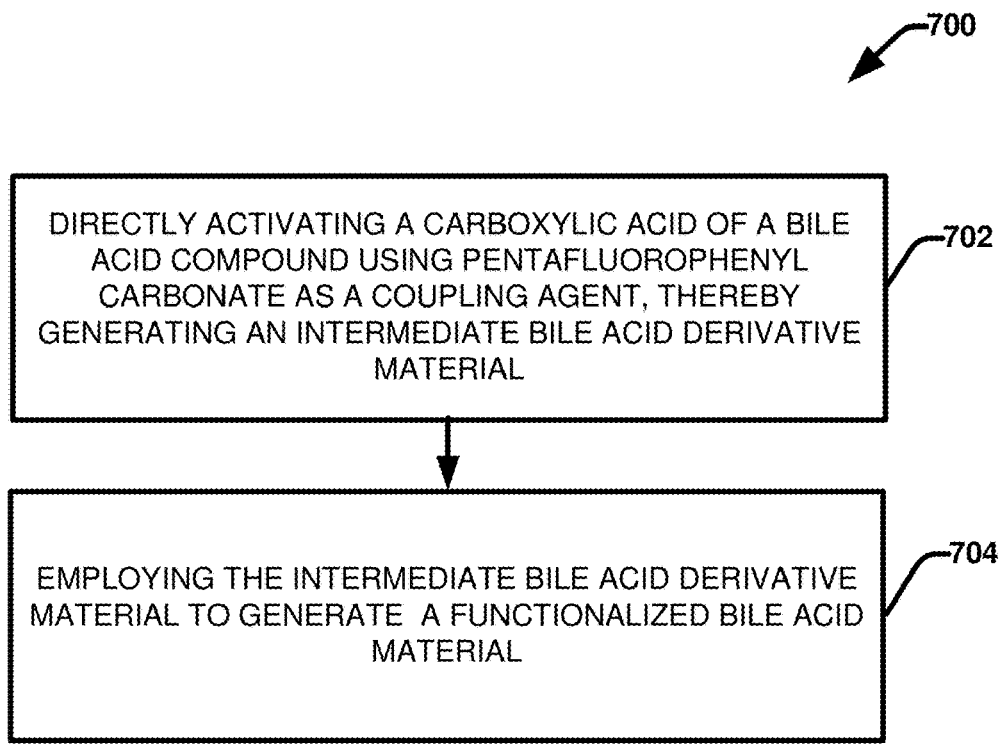
FIG. 7 provides an example, non-limiting method of generating functionalized bile acid materials in accordance with various aspects and embodiments described herein.

FIG. 7 provides an example method 700 for generating functionalized bile acid materials in accordance with various aspects and embodiments described herein. At 702, a carboxylic acid of a bile acid compound can be directly activated using pentafluorophenyl carbonate as a coupling agent, thereby generating an intermediate bile acid derivative material (e.g., pentafluorophenyl ester 2C). At 704, the intermediate bile acid derivative material can be employed to generate a functionalized bile acid material (e.g., a functionalized bile acid materials having Structure I, Structure II, or Structure III, described herein).

Figure 8:
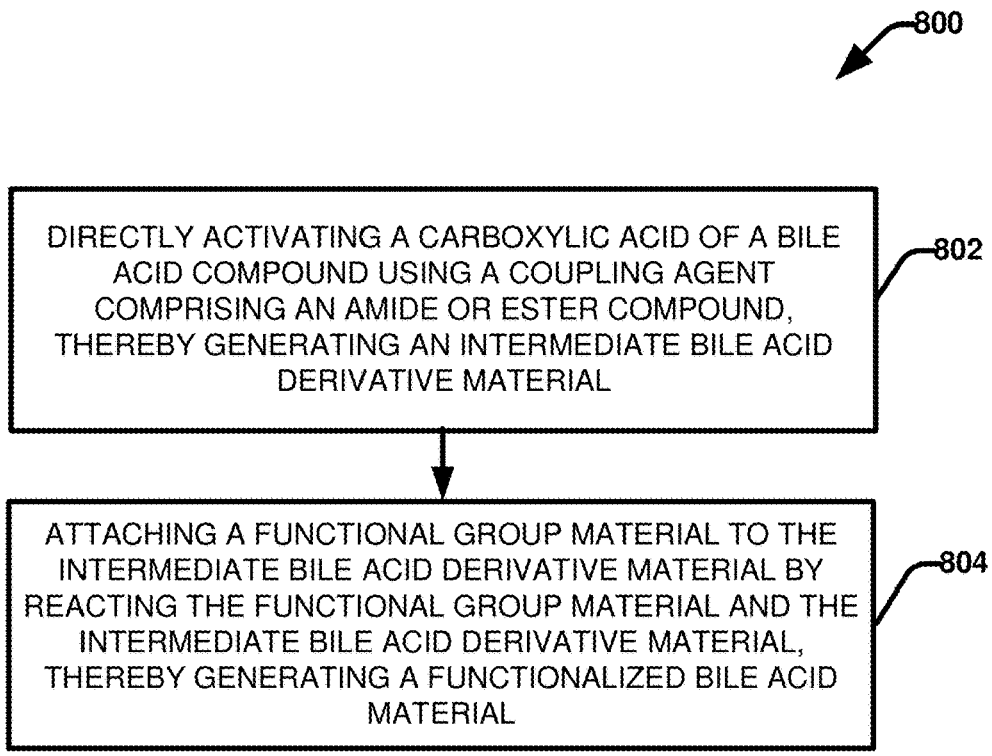
FIG. 8 provides an example, non-limiting method of generating functionalized bile acid materials in accordance with various aspects and embodiments described herein.

FIG. 8 provides an example method 800 for generating functionalized bile acid materials in accordance with various aspects and embodiments described herein. At 802, a carboxylic acid of a bile acid compound can be directly activated using a coupling agent comprising an amide or ester compound, thereby generating an intermediate bile acid derivative material (e.g., pentafluorophenyl ester 2C). At 804, a functional group material (e.g., a small molecule amine, a macromolecular amine, and the like) can be attached to the intermediate bile acid derivative material by reacting the functional group material and the intermediate bile acid derivative material, thereby generating a functionalized bile acid material (e.g., a functionalized bile acid material comprising Structure I).

Figure 9:
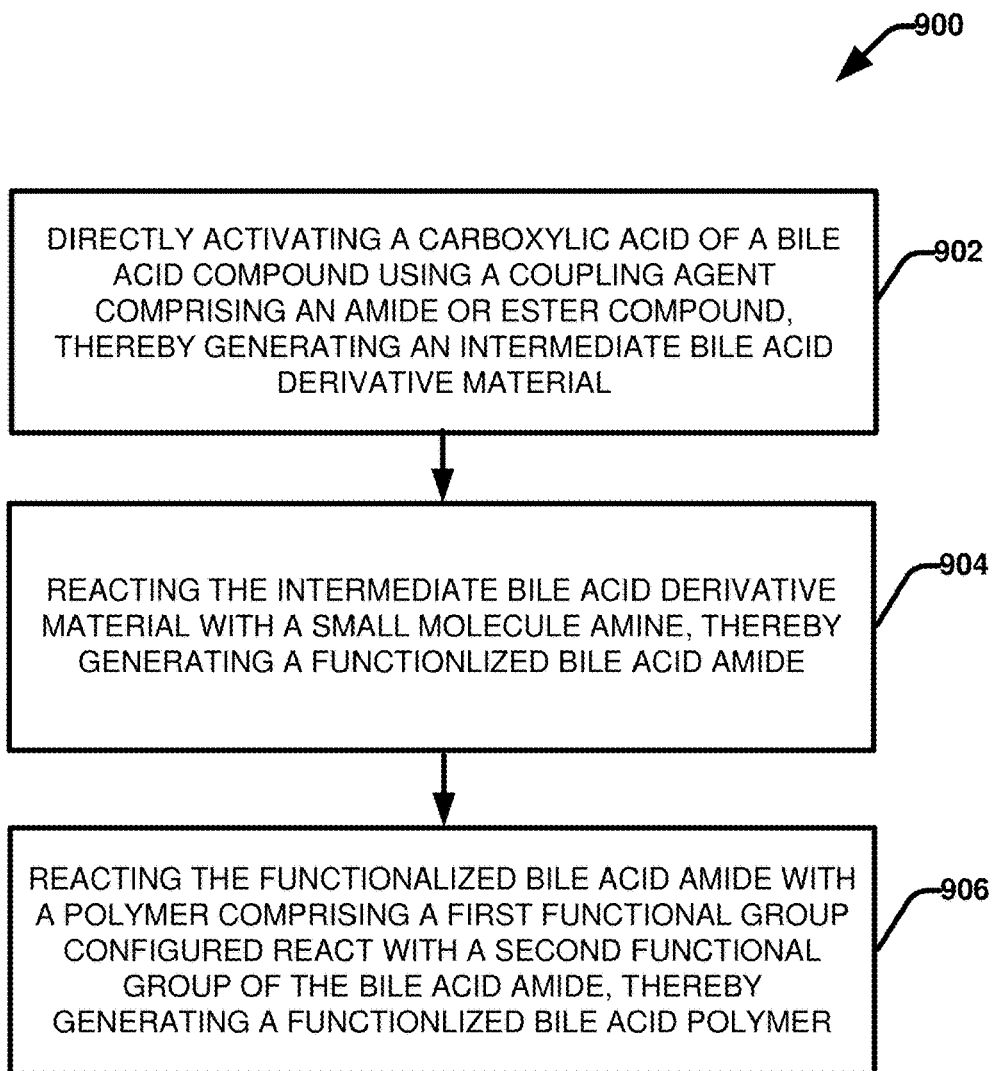
FIG. 9 provides an example, non-limiting method of generating functionalized bile acid materials in accordance with various aspects and embodiments described herein.

FIG. 9 provides an example method 900 for generating functionalized bile acid materials in accordance with various aspects and embodiments described herein. At 902, a carboxylic acid of a bile acid compound can be directly activated using a coupling agent comprising an amide or ester compound, thereby generating an intermediate bile acid derivative material (e.g., pentafluorophenyl ester 2C). At 904, a small molecule amine can be reacted with the intermediate bile acid derivative material, thereby generating a functionalized bile acid amide (e.g., a bile acid amide 3C). At 906, the functionalized bile acid amide can be reacted with a polymer comprising a first functional group configured to react with a second functional group of the bile acid amide, thereby generating a functionalized bile acid polymer (e.g., functionalized bile acid polymer comprising Structures II and/or III).

Figure 10:
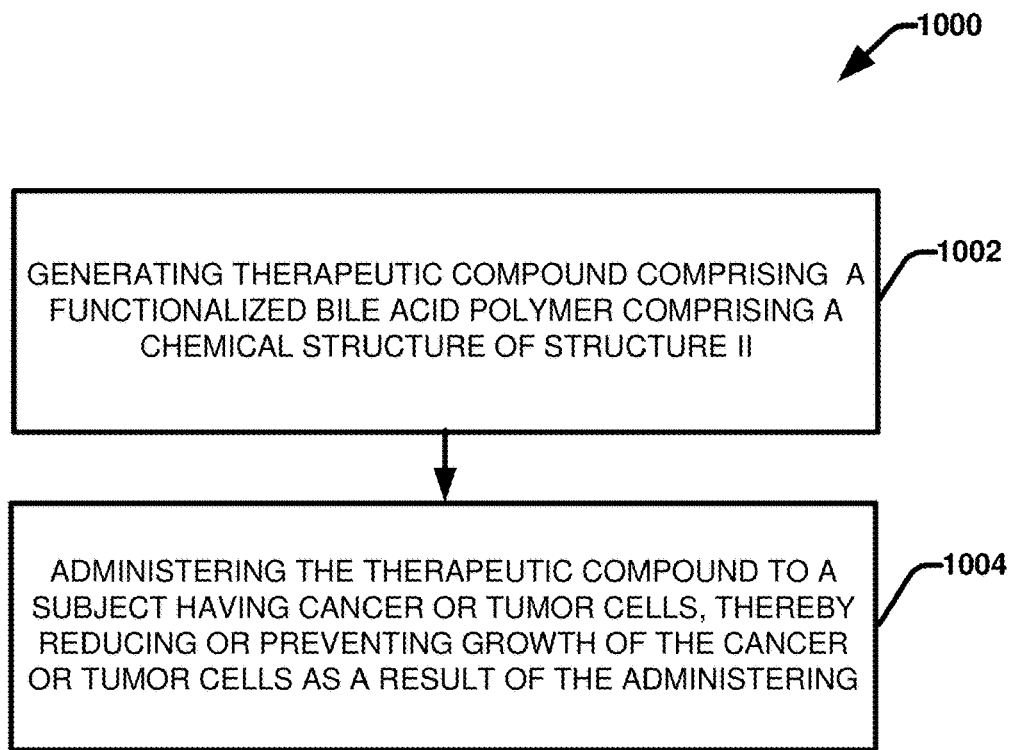
FIG. 10 provides an example, non-limiting method of treating a subject having cancer in accordance with various aspects and embodiments described herein.

FIG. 10 provides an example method 1000 for treating a subject having cancer in accordance with various aspects and embodiments described herein. At 1002, a therapeutic compound can be generated that comprises a functionalized bile acid polymer comprising a chemical structure of Structure II as defined herein. At 1004, the therapeutic compound can be administered to a subject having cancer or tumor cells, thereby reducing or preventing growth of the cancer or tumor cells as a result of the administering.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In this regard, with respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A functionalized bile acid material comprising a chemical structure of Structure I:

Structure I wherein R corresponds to a steroid backbone of a bile acid selected from the group consisting of cholic acid, deoxycholic acid, and glycocholic acid; and
wherein X corresponds to an amine nucleophilic compound selected from the group consisting of diethanolamine, N,N,N'-trimethylethylenediamine, 1-methylpiperazine, 3,3'-iminobis(N,N-dimethylpropyl amine), 2-amino-2-methyl-1,3-propanediol, (4-(aminomethyl)phenyl)boronic acid, and 1-(3-aminopropyl)imidazole, and benzylamine.

2. The functionalized bile acid material of claim 1, wherein the amine nucleophilic compound comprises a primary amine coupled to the carbonyl group of Structure I.

3. The functionalized bile acid material of claim 1, wherein the amine nucleophilic compound comprises a secondary amine coupled to the carbonyl group of Structure I.

4. The functionalized bile acid material of claim 1, wherein the bile acid is cholic acid.

5. The functionalized bile acid material of claim 1, wherein the bile acid is the deoxycholic acid.

6. The functionalized bile acid material of claim 1, wherein the bile acid is the glycocholic acid.

7. A functionalized bile acid material comprising a chemical structure of Structure I:

Structure I wherein R corresponds to a steroid backbone of a bile acid selected from the group consisting of cholic acid, deoxycholic acid, and glycocholic acid; and
wherein X corresponds to an amine nucleophilic compound selected from the group consisting of ethanolamine, N,N-dimethylethylenediamine, 1-(3-aminopropyl)imidazole, benzylamine, and 2-amino-2-methylpropane-1,3-diol.

8. The functionalized bile acid material of claim 7, wherein the amine nucleophilic compound comprises a primary amine coupled to the carbonyl group of Structure I.

9. The functionalized bile acid material of claim 7, wherein the amine nucleophilic compound comprises a secondary amine coupled to the carbonyl group of Structure I.

10. The functionalized bile acid material of claim 7, wherein the bile acid is cholic acid.

11. The functionalized bile acid material of claim 7, wherein the bile acid is the deoxycholic acid.

12. The functionalized bile acid material of claim 7, wherein the bile acid is the glycocholic acid.

13. A functionalized bile acid material comprising a chemical structure of Structure I:

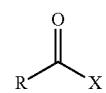

Structure I wherein R corresponds to a steroid backbone of a bile acid selected from the group consisting of cholic acid, deoxycholic acid, and glycocholic acid; and
wherein X corresponds to an amine nucleophilic compound comprising a primary amine or a secondary amine coupled to the carbonyl group of Structure I.

14. The functionalized bile acid material of claim 13, wherein the amine nucleophilic compound is selected from the group consisting of diethanolamine, N,N,N'-trimethylethylenediamine, 1-methylpiperazine, 3,3'-iminobis(N,N-dimethylpropyl amine), 2-amino-2-methyl-1,3-propanediol, (4-(aminomethyl)phenyl)boronic acid, and 1-(3-aminopropyl)imidazole, and benzylamine.

15. The functionalized bile acid material of claim 13, wherein the amine nucleophilic compound is selected from the group consisting of ethanolamine, N,N-dimethylethylenediamine, 1-(3-aminopropyl)imidazole, benzylamine, and 2-amino-2-methylpropane-1,3-diol.

16. The functionalized bile acid material of claim 13, wherein the bile acid is the cholic acid.

17. The functionalized bile acid material of claim 13, wherein the bile acid is the deoxycholic acid.

18. The functionalized bile acid material of claim 13, wherein the bile acid is the glycocholic acid.

19. A functionalized bile acid material comprising a chemical structure of structure selected from the group consisting of:

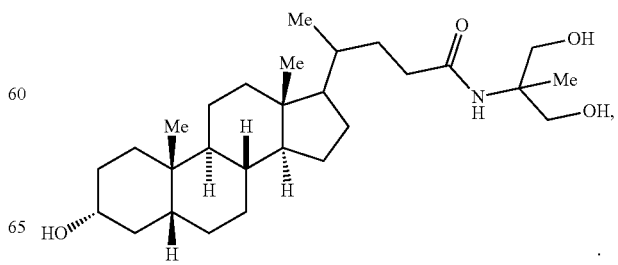

-continued
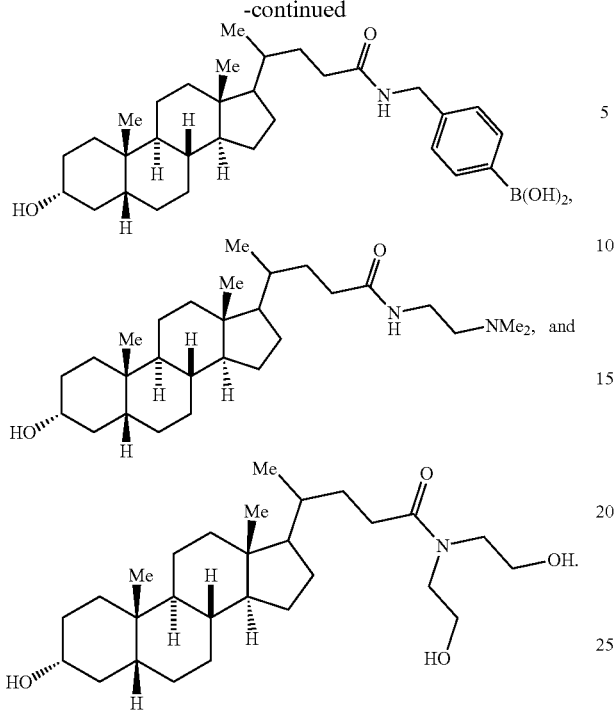
* * * * *